US00PP17918P2

(12) United States Plant Patent
Li

(10) Patent No.: US PP17,918 P2
(45) Date of Patent: Aug. 14, 2007

(54) ***VERBENA* PLANT NAMED 'KLEVE04343'**

(50) Latin Name: *Verbena hybrida*
Varietal Denomination: KLEVE04343

(75) Inventor: Ruijun Li, North Parramata (AU)

(73) Assignee: Klemm + Sohn GmbH + Co. KG., Stuttgart (DE)

( * ) Notice: Subject to any disclaimer, the term of this patent is extended or adjusted under 35 U.S.C. 154(b) by 0 days.

(21) Appl. No.: 11/343,882

(22) Filed: Jan. 31, 2006

(51) Int. Cl.
*A01H 5/00* (2006.01)

(52) U.S. Cl. ..... Plt./308

(58) Field of Classification Search ..... Plt./308
See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Verbena* plant named 'KLEVE04343', characterized by its outwardly spreading to trailing and mounded plant habit; freely branching habit; dense and bushy growth habit; and large bright pink-colored flowers with flowers held above and beyond the foliage.

1 Drawing Sheet

Botanical designation: *Verbena hybrida.*
Cultivar denomination: 'KLEVE04343'.

BACKGROUND OF THE INVENTION

The present Invention relates to a new and distinct cultivar of *Verbena* plant, botanically known as *Verbena hybrida,* and hereinafter referred by the name 'KLEVE04343'.

The new *Verbena* is a product of a planned breeding program conducted by the Inventor in Camden, New South Wales, Australia. The objective of the breeding program is to develop new compact *Verbena* cultivars with large and attractive flowers.

The new *Verbena* originated from a cross-pollination made by the Inventor in 2001 of a proprietary *Verbena hybrida* selection identified as 01.545.1, not patented, as the female, or seed, parent with a proprietary selection of *Verbena hybrida* identified as code number 01.603.1, not patented, as the male, or pollen, parent. The cultivar KLEVE04343 was discovered and selected by the Inventor as a flowering plant within the progeny from this cross-pollination in a controlled environment in Camden, New South Wales, Australia in 2002.

Asexual reproduction of the new cultivar by terminal cuttings in a controlled environment in Camden, New South Wales, Australia since 2002, has shown that the unique features of this new *Verbena* are stable and reproduced true to type in successive generations of asexual reproduction.

SUMMARY OF THE INVENTION

The following traits have been repeatedly observed and are determined to be the unique characteristics of 'KLEVE04343'. These characteristics in combination distinguish 'KLEVE04343' as a new and distinct cultivar:

1. Compact and trailing plant habit.
2. Freely branching habit; dense and bushy growth habit.
3. Large bright pink-colored flowers with flowers held above and beyond the foliage.

Plants of the new *Verbena* differ primarily from plants of the female parent selection in flower color as plants of the female parent selection have lavender-colored flowers. In addition, plants of the new *Verbena* and the female parent selection differ in leaf shape.

Plants of the new *Verbena* differ primarily from plants of the male parent selection in flower color as plants of the male parent selection have purple-colored flowers.

Plants of the new *Verbena* can be compared to plants of the cultivar Balazdapima, disclosed in U.S. Plant Pat. No. 17,292. In side-by-side comparisons conducted in Camden, New South Wales, Australia, plants of the new *Verbena* differed from plants of the cultivar Balazdapima in the following characteristics:

1. Plants of the new *Verbena* had larger leaves than plants of the cultivar Balazdapima.
2. Plants of the new *Verbena* had larger flowers than plants of the cultivar Balazdapima.
3. Plants of the new *Verbena* and the cultivar Balazdapima differed in flower color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Verbena.* The photograph comprises a side perspective view of typical flowering plants of 'KLEVE04343'.

DETAILED BOTANICAL DESCRIPTION

The cultivar KLEVE04343 has not been observed under all possible environmental conditions. The phenotype may vary somewhat with variations in environment such as temperature and light intensity without, however, any variance in genotype. The aforementioned photograph and following observations and measurements describe plants grown in Stuttgart, Germany, under commercial practice during the spring in a glass-covered greenhouse with day temperatures ranging from 18° C. to 20° C., night temperatures ranging from 15° C. to 18° C. and light levels ranging from 20,000 to 55,000 lux. Plants were about five months old when the photograph and description were taken. Plants were pinched one time. In the following description, color references are made to The Royal Horticultural Society Colour Chart, 1995 Edition, except where general terms of ordinary dictionary significance are used.

Botanical classification: *Verbena hybrida* cultivar KLEVE04343.

Parentage:

*Female, or seed, parent.*—Proprietary *Verbena hybrida* selection identified as 01.545.1, not patented.

*Male, or pollen, parent.*—Proprietary *Verbena hybrida* selection identified as code number 01.603.1, not patented.

Propagation:

*Type cutting.*—Terminal cuttings.

*Time to initiate roots, summer.*—About 5 to 8 days at 20° C.

*Time to initiate roots, winter.*—About 8 to 10 days at 20° C.

*Time to produce a rooted cutting or liner, summer.*—About 14 to 20 days at 20° C.

*Time to produce a rooted cutting or liner, winter.*—About 21 days at 20° C.

*Root description.*—Fine, fibrous; pale white in color.

*Rooting habit.*—Medium branching; moderately dense.

Plant description:

*Form.*—Compact and trailing plant habit.

*Growth and branching habit.*—Moderately vigorous and freely-branching with lateral branches potentially developing at every node; dense and bushy growth habit.

*Plant height.*—About 20 cm to 25 cm.

*Plant diameter or spread.*—About 40 cm.

*Lateral branches.*—Length: About 15 cm to 25 cm. Diameter: About 2.5 mm. Internode length: About 2.5 cm to 4 cm. Texture: Slightly pubescent. Strength: Moderately strong. Color: 138B.

*Foliage description.*—Arrangement: Opposite, simple. Length: About 1.5 cm to 3 cm. Width: About 1.2 cm to 2.5 cm. Shape: Deeply dissected. Apex: Acute. Base: Attenuate. Margin: Deeply dissected. Texture, upper and lower surfaces: Slightly pubescent. Venation pattern: Pinnate. Color: Developing and fully expanded foliage, upper surface: 138B; venation, 138C. Developing and fully expanded foliage, lower surface: 138C; venation, 138C. Petiole length: About 5 mm to 10 mm. Petiole diameter: About 1 mm. Petiole texture, upper and lower surfaces: Slightly pubescent. Petiole color, upper and lower surfaces: 138B.

Flower description:

*Flower type and habit.*—Single upright salverform flowers arranged on compact terminal racemes; flowers sessile. Freely flowering with about 12 to 15 flowers per raceme. Inflorescences positioned above and beyond the foliage. Flowers last about one week under greenhouse conditions. Flowers not persistent.

*Fragrance.*—Faint.

*Flowering season.*—In the garden, flowering is continuous from spring through the fall.

*Inflorescence height.*—About 3 cm to 5 cm.

*Inflorescence diameter.*—About 4 cm to 6 cm.

*Flower size.*—Diameter: About 1.5 cm. Depth: About 5 mm.

*Flower buds.*—Length: About 2 mm to 15 mm. Diameter: About 2 mm. Shape: Tubular, columnar. Color: 138C.

*Petals.*—Quantity/arrangement: Five per flower fused at base. Lobe length: About 5 mm to 15 mm. Lobe width: About 5 mm. Shape: Obovate. Apex: Rounded. Margin: Entire. Texture, upper and lower surfaces: Smooth, glabrous; velvety. Color: When opening, upper surface: 63B. When opening, lower surface: 63C. Fully opened, upper surface: 62B; color becoming closer to 70C with development. Fully opened, lower surface: 62C.

*Sepals.*—Quantity/arrangement: Five, fused into a tube. Length: About 1 cm. Diameter: About 1 mm. Shape: Lanceolate. Apex: Acute. Base: Attenuate. Margin: Entire. Texture, upper and lower surfaces: Coarse, pubescent. Color, upper surface: 138B. Color, lower surface: 138C.

*Peduncles.*—Length: About 5 cm. Diameter: About 1.5 mm. Strength: Strong. Color: Close to 138B.

*Reproductive organs.*—Stamens: Quantity per flower: Four, adnate to pistil. Anther shape: Elliptic. Anther length: About 1 mm. Anther color: 1C. Pollen amount: Scarce. Pollen color: 1C. Pistils: Quantity per flower: One. Pistil length: About 1.5 cm. Stigma shape: Spherical. Stigma color: 139C. Style length: About 1.5 cm. Style color: 139D. Ovary color: 139C.

*Fruit/seed.*—Fruit and seed production has not been observed.

Disease/pest resistance: Plants of the new *Verbena* have not been observed to be resistant to pathogens and pests common to *Verbena*.

Temperature tolerance: Plants of the new *Verbena* have been observed to be tolerant to temperatures ranges from about 1° C. to about 35° C.

It is claimed:

1. A new and distinct cultivar of *Verbena* plant named 'Kleve04343', as illustrated and described.

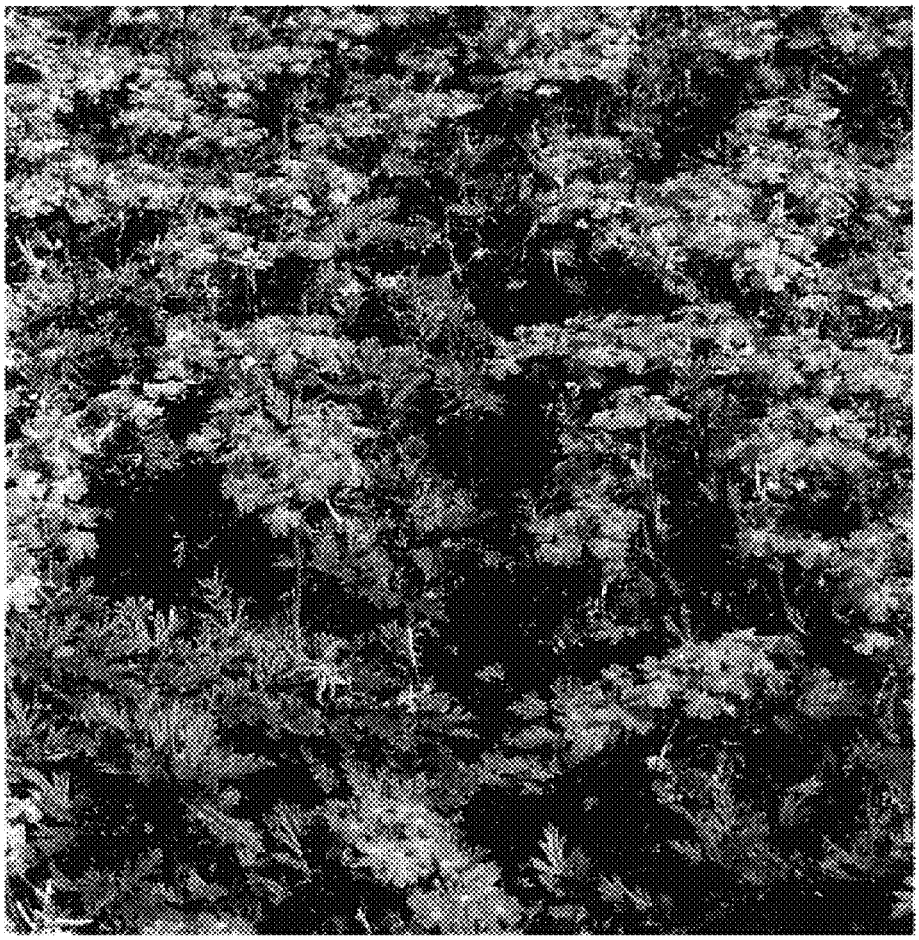

* * * * *